United States Patent [19]
Gardlik et al.

[11] Patent Number: 6,147,037
[45] Date of Patent: *Nov. 14, 2000

[54] FRAGRANCE DELIVERY SYSTEMS

[75] Inventors: John Michael Gardlik, Cincinnati; Mark Robert Sivik, Fairfield, both of Ohio

[73] Assignee: The Procter & Gamble Company, Cincinnati, Ohio

[*] Notice: This patent is subject to a terminal disclaimer.

[21] Appl. No.: 09/242,625

[22] PCT Filed: Aug. 19, 1997

[86] PCT No.: PCT/US97/14543

§ 371 Date: Feb. 19, 1999

§ 102(e) Date: Feb. 19, 1999

[87] PCT Pub. No.: WO98/07405

PCT Pub. Date: Feb. 26, 1998

Related U.S. Application Data

[60] Provisional application No. 60/024,117, Aug. 19, 1996.
[51] Int. Cl.$^7$ .......................................................... C11D 3/20
[52] U.S. Cl. .............................. 510/107; 510/106; 512/27
[58] Field of Search ............................. 512/27; 510/101, 510/106, 107

[56] References Cited

U.S. PATENT DOCUMENTS

| | | | |
|---|---|---|---|
| 4,433,695 | 2/1984 | Hall et al. | 131/276 |
| 5,668,102 | 9/1997 | Severns et al. | 510/504 |

FOREIGN PATENT DOCUMENTS 5-202378  10/1993  Japan .

*Primary Examiner*—John R. Hardee
*Attorney, Agent, or Firm*—Richard S. Echler, Sr.; Kim W. Zerby; Jacobus C. Rasser

[57] ABSTRACT

The present invention relates to a fragrance delivery system which comprises one or more pro-accords, preferably β-ketoester pro-accords, which are capable of releasing mixtures of fragrance raw materials. The pro-accords which comprise the fragrance delivery systems are useful in delivering sustained fragrances to personal care items inter alia deodorants, body lotions or creams, sun tan lotions, shampoos, as well as liquid and granular laundry detergent compositions and hard surface cleaners.

5 Claims, No Drawings

FRAGRANCE DELIVERY SYSTEMS

This application claims priority under Title 35, United States Code 119(e) from Provisional Application Ser. No. 60/024,117, filed Aug. 19, 1996.

FIELD OF THE INVENTION

The present invention relates to fragrance delivery systems suitable for use in personal care and personal hygiene articles, colognes, lotions, laundry detergent compositions, and hard surface cleaning compositions. The fragrance delivery systems comprise one or more pro-accord molecules, each molecule capable of releasing one or more fragrance raw materials. In addition, each pro-accord is capable of releasing a different accord (mixture of fragrance raw materials) if used in a different type of composition (i.e. laundry detergent vs. roll-on deodorant).

BACKGROUND OF THE INVENTION

Humans have applied scents and fragrances to their skin since antiquity and have used fragrances and scents to enhance the aesthetic quality of their environment inter alia clothing and living space. Originally these aesthetically pleasing materials were commonly isolated in raw form as resins, gums or essential oils from natural sources, inter alia, the bark, roots, leaves and fruit of indigenous plants. These resins, gums, and oils were directly applied to the body or diluted with water or other solvent, including in some cases, wine. With the advent of modem chemistry, individual components responsible for the odor properties of these resins, gums and oils were isolated and subsequently characterized. Aside from common "perfiune vehicles" inter alia, fine perfumes, colognes, eau de toilettes, after-shave lotions, and a wide variety of personal care or personal hygiene items, fragrances and scents are also delivered to clothing during the laundering process.

It is well known that mixtures of perfume or fragrance raw materials when deposited on a surface lose intensity and may change character with time, mainly due to factors such as differential evaporation and surface penetration. Many attempts have been made to minimize these drawbacks, but so far without notable success. Particularly, efforts have been made to prolong the diffusion, as well as to improve other characteristics of fragrance materials, by e.g. increasing the fragrance raw material concentration or by using additives such as silicones, glycerol, polyethylene glycols and so on. Such additions, however, have never been adequate to increase the longevity of the fragrance odor.

Accordingly, there remains a need in the art for a fragrance delivery system which can be formulated into any type of product used to deliver an aesthetically pleasing fragrance inter alia personal care and personal hygiene products, and laundry detergent compositions including rinse and dryer-added adjuncts. In addition, the delivered fragrance must have a sustained perception, therefore, the fragrance must be slowly released.

BACKGROUND ART

The following relate to the subject matter of fragrance ingredients. U.S. Pat. No. 5,626,852 Suffis et al, issued May 6, 1997; U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al, issued Dec. 18, 1973; JP 07-179,328 published Jul. 18, 1995; JP 05-230496 published Sep. 7, 1993; WO 96/38528 published Dec. 5, 1996; WO 96/14827 published May 23, 1996; WO 95/04809 published Feb. 16, 1995; and WO 95116660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention meets the aforementioned needs in that it has been surprisingly discovered that a mixture of perfume or fragrance raw materials (accords) can be released from one precursor pro-accord molecule and that these pro-accords can serve as a fragrance delivery system wherein a varying mixture of the fragrances are released depending upon the structure and design of the pro-accord molecule. These pro-accords provide sustained perfume and fragrance retention when applied to human skin either directly or by way of a personal care or personal hygiene article, said personal care and personal hygiene articles include inter alia deodorants, body lotions or creams, ointments, balms, salves, antiseptics, suntan lotions, or shampoos. In addition, the pro-accords of the present invention can be delivered to fabric wherein after the laundry cycle is complete, the pro-accords release fragrance raw materials. The pro-accords described herein comprise fragrances in a stable, releasable "pro-fragrance" form. In addition, the formulator can design compounds according to the present invention which can deliver different fragrance raw material depending upon the conditions of use. The pro-accords can be formulated into any product deliverable, directly or indirectly, to human skin, clothing, or hard surfaces upon which an aesthetically pleasing scent is desired. Once in contact with human skin, fabric, or a surface, the pro-accord is converted to a fragrance raw material mixture at a rate which provides extended fragrance benefits. The fragrance delivery systems of the present invention can be a mixture of any number of pro-accords and can cover any fragrance "characteristic" or desired fragrance volatility.

The first aspect of the present invention relates to compositions which are applied to skin, fabric, or hard surfaces, said compositions having increased fragrance retention and fragrance longevity. The suitable compositions of the present invention are inter alia deodorants, body lotions or creams, sun tan lotions, shampoos, granular and liquid laundry detergent compositions, rinse-added and dryer-added fabric softeners, and hard surface cleaners, comprising one or more pro-accord compounds having the formula:

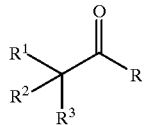

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

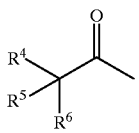

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof.

The compositions of the present invention comprise at least about 0.01%, preferably from about 0.01% to about 15%, more preferably from about 1% to about 5%, most preferably from about 0.1% to about 1% by weight, of one or more β-ketoesters described herein.

The present invention also relates to the use of the fragrance delivery system of the present invention to release fragrance accords when pro-accords are applied to a situs whether the pro-accords are delivered by a vehicle or carrier. The vehicle or carrier may be a liquid such as water, or an article which comprises a β-ketoester pro-accord and in treated with an agent which catalyzes the release of the fragrance raw materials. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to a fragrance delivery system which lays down one or more fragrance "pro-accord" compounds onto skin, hair, fabric, ceramic tile, linoleum, or other substrate during usage or which can be applied to an article of manufacture wherein the pro-accord is activated to release one or more fragrance raw materials. Because the pro-accords which comprise the fragrance delivery system of the present invention generally have a higher molecular weight than uncombined fragrance raw materials and other "pro-fragrance-type" compounds (i.e. pro-fragrances which only deliver a single equivalent of a fragrance raw material), they are a means for effectively delivering two or more fragrance raw materials which results in enhanced longevity of the fragrance raw materials on a substrate.

Mixtures of fragrance materials are known by those skilled in the art of fragrances and perfumes as "accords". The term "accord" as used herein is defined as "a mixture of two or more 'fragrance raw materials' which are artfully combined to impart a pleasurable scent, odor, essence, or fragrance characteristic". For the purposes of the present invention "fragrance raw materials" are herein defined as compounds imparting an odor, fragrance, essence, or scent either alone or in combination with other "fragrance raw materials" which is considered aesthetically pleasing, preferably said compounds have a molecular weight of at least 100 g/mol.

For the purposes of the present invention the term "pro-fragrance" is defined as "a β-ketoester which releases a fragrance raw material alcohol" whereas a "pro-accord" is defined as "β-ketoester which release two or more fragrance raw materials". For the purposes of the present invention, however, since a material that is a "pro-fragrance" in one embodiment can serve as a "pro-accord" in a different embodiment, the term "pro-fragrance" is used interchangeably with the term "pro-accord" and either term may be used to stand equally well for either β-ketoester pro-fragrance molecules, β-ketoester pro-accord molecules, or both collectively.

Typically "fragrance raw materials" comprise inter alia alcohols, ketones, aldehydes, esters, ethers, nitriles, and cyclic and acyclic alkenes, especially terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Muller, P. M. and Lamparsky, D., Blackie Academic and Professional (1994) both incorporated herein by reference.

For example, but not by way of limitation, the fragrance accords released by the pro-accords of the present invention have a "heart", "character", or "note" which is described as inter alia rose, jasmin, lilac, lily of the valley, violet, orange, peach, watermelon, and lemon, or the pro-accord can deliver fragrance raw materials which provide a "fresh" or "clean" note, for example, linalool or dihydromyrcenol. The accord may be further "modified" or "twisted" by the inclusion of pro-accords which deliver modifier top or middle notes which, as an additional benefit afforded by the present invention, can be incorporated into the pro-accord. For example, a "rose essence" may be combined with a "green" modifier to "shift the fragrance accord character".

For the purposes of the present invention, only fragrance raw materials having a molecular weight of at least 100 g/mol are considered "preferred fragrance raw materials" according to the present invention. Therefore, low molecular weight materials inter alia methanol, ethanol, methyl acetate, ethyl acetate, and methyl formate which are common components of fragrance accords are less preferred fragrance raw materials However, the formulator may wish to deliver these lower molecular weight materials (less than a molecular weight of 100 g/mol) as carriers, astringents, diluents, balancers, fixatives, or as other suitable adjunct materials.

For the purposes of the present invention "top note" fragrance raw materials are defined as "fragrances having a high vapor pressure, and when applied to a paper sachet, vaporization takes place within 2 hours, and no scent remains; essentially, the initial impression of the perfume formulation is provided by top notes".

For the purposes of the present invention "middle note" fragrance raw materials are defined as "fragrances having a medium vapor pressure, and when applied to a paper sachet, the scent remains from about 2 to about 6 hours; essentially, middle notes provide the skeleton of the perfume formulation".

For the purposes of the present invention "base note" fragrance raw materials are defined as "fragrances having a low vapor pressure and high retentivity, and when applied to a paper sachet, the scent remains for more than about 6 hours; essentially, base notes provide the characteristic of the perfume formulation.

The terms "top note", "middle note", and "base note" are well recognized by those skilled in the art of fragrance-containing compositions. However, reference to a specific fragrance raw material as a "top note" within the present invention does mean that others skilled in the art of fragrance-containing compositions may not categorized the same ingredient as a "middle note". The same applies to fragrance raw materials referred to as "middle notes" and "base notes".

Pro-Accords

The fragrance delivery systems of the present invention comprise one or more pro-accords having the formula:

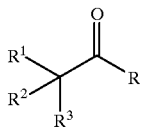

wherein R is alkoxy derived from a fragrance raw material alcohol. Non-limiting examples of preferred fragrance raw material alcohols include 2,4-dimethyl-3-cyclohexene-1-methanol (Floralol), 2,4-dimethyl cyclohexane methanol (Dihydro floralol), 5,6-dimethyl-1-methylethenylbicyclo [2.2.1]hept-5-ene-2-methanol (Arbozol), α,α,-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3-dimethyl-$\Delta^2$-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, 1-phenylpropanol, 3-phenylpropanol, 2-phenylpropanol (Hydrotropic Alcohol), 2-(cyclododecyl) propan-1-ol (Hydroxy-ambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo [2.2.1.0$^{(2,6)}$]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-isopropenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl) cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1] hept-2-ene (myrtenol), 4-methyl-2,4-heptadien-1-ol, 3,4,5, 6,6-pentamethyl-2-heptanol, 3,6-dimethyl-3-vinyl-5-hepten-2-ol, 6,6-dimethyl-3-hydroxy-2-methylenebicyclo [3.1.1]heptane, 1,7,7-trimethylbicyclo[2.2.1]heptan- 2-ol, 2,6-dimethylheptan-2-ol (dimetol), 2,6,6-trimethylbicyclo [1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (curninyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyloctahydro-2-naphthol, 1,3,3-trimethyl-2-norbomanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetrahydrofuran, β-caryophyllene alcohol, vanillin and mixtures thereof.

More preferably, the fragrance raw material alcohol is selected from the group consisting of cis-3-hexen-1-ol, hawthanol [admixture of 2-(o-methylphenyl)-ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(1-methylethyl)cyclohexane methanol, 3-(hydroxy-methyl)-2-nonanone, octan-1-ol, 3-phenylpropanol, Rhodinol 70 [3,7-dimethyl-7-octenol, 3,7-dimethyl-6-octenol admixture], 9-decen-1-ol, α-3,3-trimethyl-2-norborane methanol, 3-cyclohexylpropan-1-ol, 4-methyl-1-phenyl-2-pentanol, 3,6-dimethyl-3-vinyl-5-hepten-2-ol, phenyl ethyl methanol; propyl benzyl methanol, 1-methyl-4-isopropenylcyclohexan-3-ol, 4-isopropyl-1-methylcyclohexan-3-ol (menthol), 4-tert-butylcyclohexanol, 2-tert-butyl-4-methylcyclohexanol, 4-isopropylcyclo-hexanol, trans-decahydro-β-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy-4-(1-propenyl)phenol, vanillin, ethyl vanillin, and mixtures thereof.

$R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

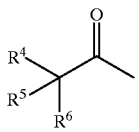

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof.

Preferably at least two $R^1$, $R^2$, or $R^3$ units are hydrogen. In one embodiment of the present invention preferably $R^4$, $R^5$, and $R^6$ units are each hydrogen. In addition, preferably when two $R^4$, $R^5$, and $R^6$ units are hydrogen, the remaining unit is $C_1$–$C_{20}$ substituted or unsubstituted linear alkyl, $C_3$–$C_{20}$ substituted or unsubstituted branched alkyl, $C_3$–$C_{20}$ substituted or unsubstituted cyclic alkyl; more preferably methyl. Also preferably $R^4$, $R^5$, and $R^6$ are taken together to form a $C_6$–$C_{30}$ substituted or unsubstituted aryl unit, preferably substituted or unsubstituted phenyl and naphthyl.

For the purposes of the present invention the term "substituted" as it applies to linear alkyl, branched alkyl, cyclic alkyl, linear alkenyl, branched alkenyl, cyclic alkenyl, branched alkoxy, cyclic alkoxy, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_3$–$C_{12}$ branched alkoxy, preferably isopropoxy; $C_3$–$C_{12}$ cyclic alkoxy; nitrilo; halogen, preferably chloro and bromo, more preferably chloro; nitro; morpholino; cyano; carboxyl, non-limiting examples of which are —CHO; —CO$_2$—M$^+$, —CO$_2$R$^9$; —CONH$_2$; —CONHR$^9$; —CONR$^9{}_2$; wherein R$^9$ is $C_1$–$C_{12}$ linear or branched alkyl); —SO$_3$—M$^+$; —OSO$_3$—M$^+$; —N(R$^{10}$)$_2$; and —N$^+$(R$^{10}$)$_3$X$^-$ wherein each R$^{10}$ is independently hydrogen or $C_1$–$C_4$ alkyl; and mixtures thereof; wherein M is hydrogen or a water soluble cation; and X is chlorine, bromine, iodine, or other water soluble anion.

For the purposes of the present invention substituted or unsubstituted alkyleneoxy units are defined as moieties having the formula:

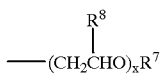

wherein $R^7$ is hydrogen; $R^8$ is hydrogen, methyl, ethyl, and mixtures thereof; the index x is from 1 to about 10.

For the purposes of the present invention substituted or unsubstituted alkyleneoxyalkyl are defined as moieties having the formula:

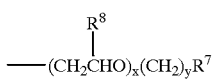

wherein $R^7$ is hydrogen, $C_1$–$C_{18}$ alkyl $C_1$–$C_4$ alkoxy, and mixtures thereof; $R^8$ is hydrogen, methyl, ethyl, and mixtures thereof; the index x is from 1 to about 10 and the index y is from 2 to about 18.

For the purposes of the present invention substituted or unsubstituted aryl units are defined as phenyl moieties having the formula:

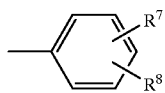

or α and β-naphthyl moieties having the formula:

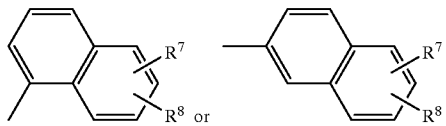

wherein $R^7$ and $R^8$ can be substituted on either ring, alone or in combination, and $R^7$ and $R^8$ are each independently hydrogen, hydroxy, $C_1$–$C_6$ alkyl, $C_2$–$C_6$ alkenyl, $C_1$–$C_4$ alkoxy, $C_3$–$C_6$ branched alkoxy, nitrilo, halogen, nitro, morpholino, cyano, carboxyl (—CHO; —$CO_2$—$M^+$; —$CO_2R^9$; —$CONH_2$; —$CONHR^9$; —$CONR^9{}_2$; wherein $R^9$ is $C_1$–$C_{12}$ linear or branched alkyl), —$SO_3$—$M^+$, —$OSO_3$—$M^+$, —$N(R^{10})_2$, and —$N^+(R^{10})_3X$— wherein each $R^{10}$ is independently hydrogen, $C_1$–$C_4$ alkyl, or mixtures thereof; and mixtures thereof, $R^7$ and $R^8$ are preferably hydrogen, $C_1$–$C_6$ alkyl, —$CO_2$—$M^+$, —$SO_3$—$M^+$, —$OSO_3$—$M^+$, and mixtures thereof; more preferably $R^7$ or $R^8$ is hydrogen and the other moiety is $C_1$–$C_6$; wherein M is hydrogen or a water soluble cation and X is chlorine, bromine, iodine, or other water soluble anion. Examples of other water soluble anions include organic species such as fumarate, succinate, tartrate, oxalate and the like, inorganic species include sulfate, hydrogen sulfate, phosphate and the like.

For the purposes of the present invention substituted or unsubstituted alkylenearyl units are defined as moieties having the formula:

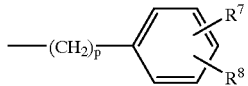

wherein $R^7$ and $R^8$ are each independently hydrogen, hydroxy, $C_1$–$C_4$ alkoxy, nitrilo, halogen, nitro, carboxyl (—CHO; —$CO_2$—$M^+$; —$CO_2R^9$; —$CONH_2$; —$CONHR^9$; —$CONR^9{}_2$; wherein $R^9$ is $C_1$–$C_{12}$ linear or branched alkyl), amino, alkylamino, and mixtures thereof, p is from 1 to about 14; M is hydrogen or a water soluble cation.

For the purposes of the present invention substituted or unsubstituted alkyleneoxyaryl units are defined as moieties having the formula:

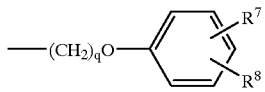

wherein $R^7$ and $R^8$ are each independently hydrogen, hydroxy, $C_1$–$C_4$ alkoxy, nitrilo, halogen, nitro, carboxyl (—CHO; —$CO_2$—$M^+$; —$CO_2R^9$; —$CONH_2$; —$CONHR^9$; —$CONR^9{}_2$; wherein $R^9$ is $C_1$–$C_{12}$ linear or branched alkyl), amino, alkylamino, and mixtures thereof, q is from 1 to about 14; M is hydrogen or a water soluble cation.

Surprisingly, the pro-accords which comprise the fragrance delivery systems of the present invention are capable of releasing at least one fragrance raw material, preferably the pro-accords release two or more fragrance raw materials.

For example, the pro-accord 3,7-dimethyl-1,6-octadien-3-yl 3-(β-naphthyl)-3-oxo-propionate having the formula:

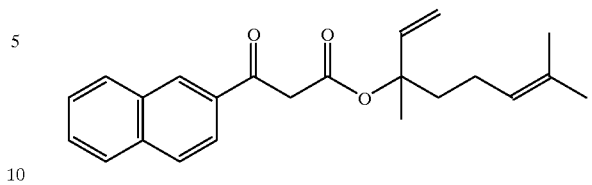

releases, depending upon usage conditions, at least two fragrance raw materials inter alia linalool, β-naphthyl methyl ketone, myrcene, α-terpinolene, and Δ-3-carene.

The pro-accords which comprise the fragrance delivery systems of the present invention are capable of releasing their fragrance compounds by more than a single chemical mechanism, a point which is key to the variety of fragrance raw materials which are released from a single pro-accord compound. Therefore, depending upon the desires of the formulator, the pro-accords of the present invention are capable of releasing a different mixture of fragrance raw materials depending upon the releasing milieu. For example, the pro-accord 3,7-dimethyl-1,6-octadien-3-yl 3-(β-naphthyl)-3-oxo-propionate produces a different accord when undergoing fragrance raw material release in water than when said pro-accord is subjected to the high temperature typical of an automatic clothes dryer or iron. Typically the pro-accords of the present invention release a mixture of alcohols, esters, ketones, hydrocarbyl materials, especially terpenes, having aesthetically pleasing qualities, and mixtures thereof. For the purposes of the present invention the term "hydrocarbyl material" is defined as a compound which essentially comprises only carbon and hydrogen inter alia alkanes, alkenes, and alkynes whether linear, cyclic, branched, or combinations thereof. An example, of a hydrocarbyl material which is capable of being released by a pro-accord of the present invention is myrcene. For the purposes of the present invention the term "terpene" is used to designate hydrocarbons inter alia myrcene, limonene, and α-terpinolene. However, those skilled in the art of perfumes as well as organic chemistry recognize that geraniol and nerol which are listed under "fragrance raw material alcohols" herein above are also terpenes. Throughout the present specification the term "terpene" is used interchangeably with "hydrocarbyl" and when "terpene" is used broadly, it refers to all alcohols, ketones, alkenes, etc. that are generally regarded as terpenes, and when the term "terpene" is used narrowly it refers primarily to alkanes, alkenes, etc. having typically 10 carbon atoms (terpenes) or 15 carbon atoms (sesquiterpenes).

The formulator may, however, adjust the conditions of use such that single fragrance raw materials are released by the pro-accord. For example, α,β-ketoester pro-accord prepared from dihydromyrcenol and capable of releasing dihydromyrcenol as well as other fragrance raw materials may be formulated into a composition which affords only the release of dihydromyrcenol until usage conditions are changed or adjusted such that the other fragrance raw materials are releasable. In addition, pro-accords may be prepared which release different fragrance raw materials under different conditions. For example, while an article of clothing is line-drying one fragrance accord is release, while a second fragrance accord is released while the article is dry and hanging in a closet.

Examples of alcohols releasable by the pro-accords are described herein above and are typically the fragrance raw material alcohols which are used to form the parent compounds. However, during the process of fragrance raw material release, these fragrance raw material alcohols are capable of undergoing further modification, including isomerization and/or rearrangement. Therefore, in addition to the original alcohol used to form the parent pro-accord ester, additional alcohols may be formed by transformations which occur during the release process. Depending upon the choices the formulator makes when designing the pro-accord molecules in formulating a fragrance delivery system according to the present invention, these transformations can take place to a greater or lesser degree.

Non-limiting examples of terpenes releasable by the pro-accords of the present invention include the hydrocarbyl materials myrcene, ocimene, β-farnesene, cis-achillene, trans-achillene, carvomenthene, limonene, α-terpinene, γ-terpinene, terpinolene, α-phellandrene, β-phellandrene, 2-carene, 3-carene, α-pinene, β-pinene, camphene, and other terpenes, for example, (−)-(2S,4R)-2-(2-methyl-1-propenyl)-4-methyltetrahydropyran (cis rose oxide), (−)-(2S,4S)-2-(2-methyl-1-propenyl)-4-methyltetrahydropyran (trans rose oxide), 2-methyl-2-vinyl-5-(α-hydroxy-isopropyl)tetrahydrofuran (linalool oxide), and mixtures thereof.

Non-limiting examples of ketones which are releasable by the pro-accords of the fragrance delivery systems of the present invention are α-damascone, β-damascone, δ-damascone, β-damascenone, muscone, 3,3-dimethylbutanone, methyl phenyl ketone (acetophenone), 4-phenylbutan-2-one (benzyl acetone), 2-acetyl-3,3-dimethyl norbornane (camek dh), 6,7-dihydro-1,1,2,3,3-pentamethyl-4(5H) indanone (cashmeran), 4-(1,3)-benzodioxol-5-yl 3-buten-2-one (cassione), 4-(3,4-methylenedioxyphenyl)-2-butanone (dulcinyl), 3-octanone, 6-acetyl-1,2,3,4-tetrahydronaphthalene ketone (florantone t), ethyl-2-n-hexyl acetoacetate (gelsbne), 2,6-dimethylundeca-2,6-dien-10-one, 6,10-dimethyl-5,9-undecadien-2-one, 3,3-dimethylcyclohexyl methyl ketone (herbac), 4-(2,6,6-trimethyl-1-cyclohexen-1-yl)-3-buten-2-one (β-ionone), 4-(2,6,6-trimethyl-2-cyclohexen-1-yl)-3-buten-2-one (α-ionone), 3-methyl-4-(2,6,6-trimethyl-1-cyclohexen-1-yl)-3-buten-2-one (δ-methyl ionone), 4-(2,6,6-trimethyl-2-cyclohexen-1-yl)-3-methyl-3-buten-2-one (γ-methyl ionone), 3-methyl-4-(2,6,-trimethyl-2-cyclohexen-1-yl)-3-buten-2-one (irisantheme), 4-(2,3,5-trimethyl4-cyclohexen-1-yl)-3-buten-2-one (iritone), 4-methyl-(2,5,6,6-tetramethyl-2-cyclohexen-1-yl)-3-buten-2-one (α-ionone), 1,2,3,4,5,6,7,8-octahydro-2,3,8,8-tetramethyl-2-acetonaphthone (iso cyclomone e), 7-acetyl-1,2,3,4,5,6,7,8-octahydro-1,1,6,7-tetramethyl naphthalene (Iso E Super®), acetyl diisoamylene (Koavone®), methyl amyl ketone, 2-acetonaphthone cedr-8-enyl methyl ketone (methyl cedrylone), 2,3,6-trimethyl-cyclohexen-4-yl-1-methyl ketone (methyl cyclo citrone), hexahydroacetophenone (methyl cyclohexyl ketone), 6-methyl-3,5-heptadien-2-one, 6-methyl-5-hepten-2-one, 2-octanoe, 3-(hydroxymethyl)-2-nonanone, 4-acetyl-1,1-dimethyl-6-tert-butyl indane (musk indanone), 2,6-dinitro-3,5-dimethyl-4-acetyl-tert-butyl benzene (musk ketone), 1-para-menthen-6-yl propanone (nerone), para-methoxy acetophenone (acetanisole), 6-acetyl-1,1,2,3,3,5-hexamethyl indan (Phantolid®), 7-acetyl-1,1,3,4,4,6-hexamethyl tetralin (Tonalid®, Musk Plus®), 5-acetyl-3-isopropyl-1,1,2,6-tetramethyl indane (Traseolide 70®), methyl-2,6,10-trimethyl-2,5,9-cyclododecatriene-1-yl ketone (Trimofix O®), methyl cedrylone (Vertofix Coeur®), 4-(4-hydroxy-3-methoxyphenyl)-2-butanone, cis-jasmone, dihydrojasmone, α-ionone, β-ionone, dihydro-β-ionone, 4-(4-hydroxyphenyl)butan-2-one, 1-carvone, 5-cyclohexadecen-1-one, decatone, 2-[2-(4-methyl-3-cyclohexenyl-1-yl) propyl]cyclopentan-2-one, 2-sec-butylcyclohexanone, allyl ionone, α-cetone, geranyl acetone, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, menthone, methyl-7,3-dihydro-2H-1,5-benzodioxepine-3-one, fenchone, methyl hydroxynaphthyl ketone, and mixtures thereof.

According to the present invention all isomers of a fragrance raw material whether in the form of the pro-accord or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R-(+)-p-citronellol and S-(−)-β-citronellol. Each of these materials separately or as a racemic pair are suitable for use as fragrance raw materials in the present invention. However, those skilled in the art of fragrances, by utilization of the present invention, should not disregard the olfactory differences that individual optical isomers, admixtures of optical isomers or admixtures of positional isomers impart. By way of example, carvone, 2-methyl-5-(1-methylethenyl)-2-cyclohexene-1-one exists as two isomers; d-carvone and l-carvone. d–Carvone is found in oil of caraway and renders a completely different fragrance from l-carvone which is found in spearmint oil. According to the present invention a pro-accord which releases d-carvone will result in a different scent or fragrance than one which releases l-carvone. The same applies to l-carvone. In addition, isomers such as cis/trans isomers, for example, nerol (3,7-dimethyl-cis-2,6-octadien-1-ol) and geraniol (3,7-dimethyl-trans-2,6-octadien-1-ol), are well known to those skilled in the art of perfumery and these two terpene alcohols, which commonly occur as an admixture, have different fragrance characteristics. Therefore, when formulating fragrance raw materials which comprise mixtures of isomers such as nerol/geraniol, the formulator must also take into account whether different sources of raw material have different ratios of isomers.

An example of a preferred pro-accord is 3,7-dimethyl-1,6-octadien-3-yl 3-(β-naphthyl)-3-oxo-propionate having the formula:

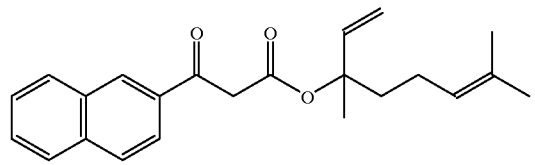

which releases at least the fragrance raw material alcohol, linalool, having the formula:

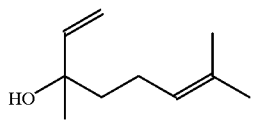

and the fragrance raw material ketone, methyl naphthyl ketone, having the formula:

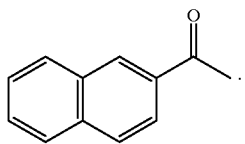

A further example of a preferred pro-accord includes 2,6-dimethyl-7-octen-2-yl 3-(4-methoxyphenyl)-3-oxo-propionate having the formula:

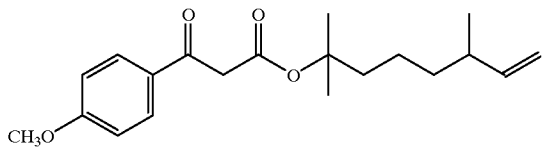

which releases at least the fragrance raw material alcohol, dihydromyrcenol, having the formula:

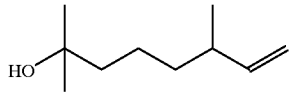

and the fragrance raw material ketone, methyl 4-methoxyphenyl ketone, having the formula:

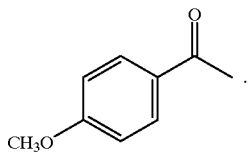

Further non-limiting examples of preferred pro-accords include 3,7-dimethyl-1,6-octadien-3-yl 3-(α-naphthyl)-3-oxo-propionate, [linalyl (1-naphthoyl)acetate], having the formula:

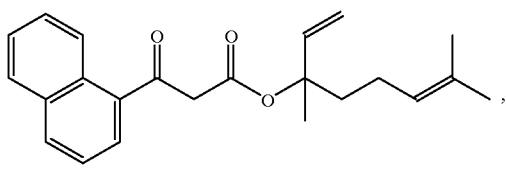

2,6-dimethyl-7-octen-2-yl 3-(4-methoxyphenyl)-3-oxo-propionate, [3-(4-methoxyphenyl)-3-oxo-propionic acid dihydromyrcenyl ester], having the formula:

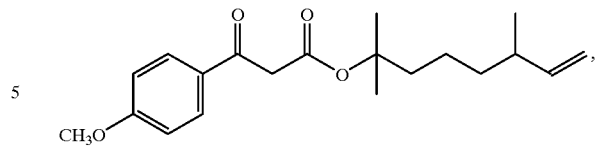

2,6-dimethyl-7-octen-2-yl 3-(4-nitrophenyl)-3-oxo-propionate, [3-(4-nitrophenyl)-3-oxo-propionic acid dihydromyrcenyl ester], having the formula:

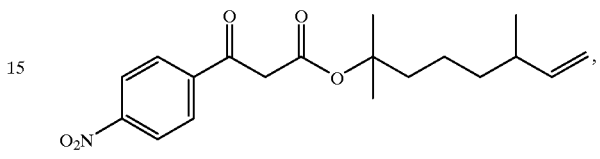

2,6-dimethyl-7-octen-2-yl 3-(β-naphthyl)-3-oxo-propionate, [dihydromyrcenyl (2-naphthoyl)acetate], having the formula:

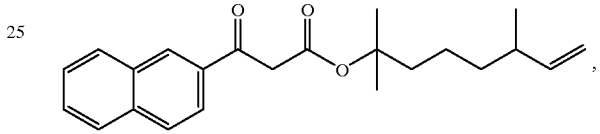

3,7-dimethyl-1,6-octadien-3-yl 3-(4-methoxyphenyl)-3-oxo-propionate, [3-(4-methoxyphenyl)-3-oxo-propionic acid linalyl ester], having the formula:

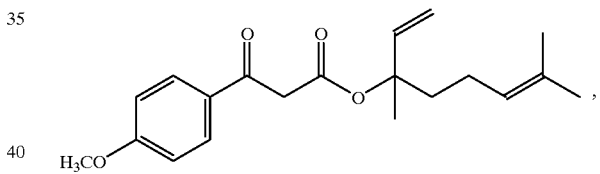

(α,α-4-trimethyl-3-cyclohexenyl)methyl 3-(β-naphthyl)-3-oxo-propionate, [α-terpinyl (2-naphthoyl)acetate], having the formula:

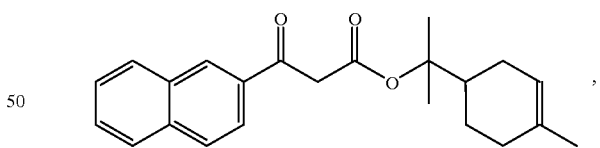

9-decen-1-yl 3-(β-naphthyl)-3-oxo-propionate, [9-decen-1-yl (2-naphthoyl)acetate], known alternatively as, rosalva 2'-acetonaphthone, having the formula:

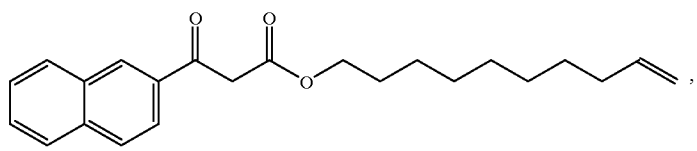

3,7-dimethyl-1,6-octadien-3-yl 3-(nonanyl)-3-oxo-propionate, [linalyl (nonanoyl)acetate], known alternatively as, octyl [(linalyl) α-acetyl] ketone, having the formula:

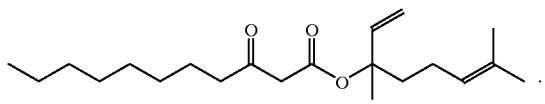

Additional non-limiting examples of preferred pro-fragrances which comprise the fragrance delivery systems of the present invention include cis 3-hexen-1-yl 3-(β-naphthyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2;2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof.

Without wishing to be limited by theory, the process by which the pro-accords of the present invention release their fragrance raw materials is not limited to one pathway. In fact, the same molecule under identical conditions may have several equal pathways by which the same or different compounds are released. For example, both nerol and geraniol may be released from an ester which is formed only from geraniol, provided the conditions under which the geraniol to nerol transformation can occur, are present during usage. These conditions can by built into the molecule by the formulator or can be provided by the surrounding environment (i.e. the formulation). In addition, during the process of fragrance raw material release, both the keto-portion and the alcohol-portion of the pro-accords are capable of undergoing chemical transformations which provide a mixture of fragrance notes not subject to inclusion in the original pro-accords. For example, a pro-accord ester which comprises the fragrance raw material alcohol citronellol, can potentially release a mixture of rose oxides by the following scheme:

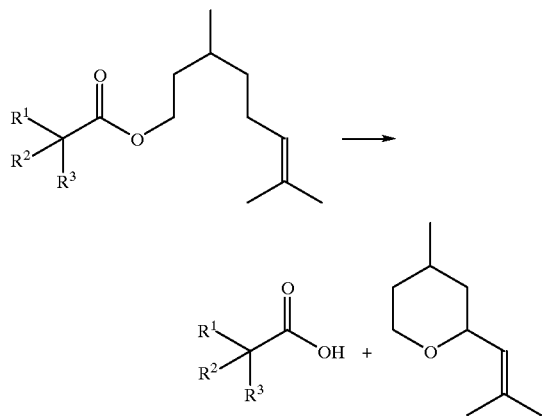

provided that suitable rearrangement conditions are present during usage.

The formulator is not limited to the delivery of one type of fragrance, for example a top, middle, or base fragrance raw material note. Instead a mixture of top notes, a mixture of top and middle notes, or any combination of top, middle and base notes may be delivered in any suitable proportion.

As described herein above, those skilled in the art of preparing fragrance-containing compositions have categorized fragrances into three types based on their relative volatility; top, middle, and base notes. In addition, fragrances are categorized by the odor they produce; some of these descriptors are broad and others are relatively specific. For example, "floral" is a term which connotes odors associated with flowers while the term "lilac" is more specific. Descriptors used by those skilled in the art of perfumes and fragrances are inter alia "rose", "floral", "green", "citrus", "spicy", "honey", and "musk". The sources of these notes are not limited to one chemical class; alcohols can produce "rose", "green", and "musk" scents, while "rose" scents can comprise alcohols, ketones, terpenes, aldehydes, etc.

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. The compositions described herein below, as well as others chosen by the formulator, comprise a fragrance delivery system which utilizes the pro-accords of the present invention to successfully deliver a "balanced fragrance" profile.

It is also recognized by those skilled in the art that descriptors which relate to aesthetic perceptions such as "top", "middle" and "base" notes are relative terms. A fragrance raw material categorized as a top note by one formulator usually has the identical classification among most other Perfumers. The same is true for the middle and base notes, however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Yet apart from this pleasant fragrance, a fragrance delivery system which is used to deliver a scent to a perfume, cologne, personal care item, laundry detergent composition or hard surface cleaner must meet a number of technical requirements. It must be sufficiently strong, it must be persistent, and it must retain its "essential character" throughout its period of evaporation.

Aside from the changes made to the pro-accord molecules for the purpose of modifying the fragrance profiles which the fragrance delivery systems of the present invention provide, modifications can be made to these pro-accords for the purpose of increasing the substantivity of the materials. The formulator by selecting a suitable $R^1$, $R^2$, or $R^3$ unit, or upon the selection of $R^4$ $R^5$, and $R^6$, can influence the degree and rate at which the pro-accord is deposited upon fabric or other surface. Those skilled in the art of formulating detergent compositions will recognize that the terms "substantive" and "substantivity" refer to the propensity of a compound to adhere to, associate with, or deposit upon a surface, preferably the surface of fabric. Therefore, compounds which are more substantive more readily adhere to fabric surface. However, substantive compounds, in general, do not react with the surface onto which they deposit.

An example of a pro-accord which is modified to provide higher fabric substantivity is the 2,6-dimethyl-7-octen-2-yl 3-(β-naphthyl)-2-(methoxy-pentaethyleneoxy)-3-oxo-propionate, [dihydromyrcenyl (2-naphthoyl)(2-$E_5$ methoxy) acetate], having the formula:

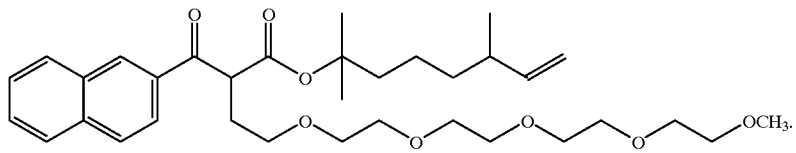

In addition to substitution at the β-carbon atom, substitution can be made at other sites of the pro-accord molecule, for example, 3,7-dimethyl-1,6-octadien-3-yl 3-(methoxy triethyleneoxy)-3-oxo-butyrate, [linalyl (methoxy E₃)acetate] having the formula:

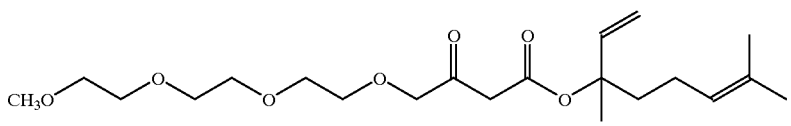

is a pro-accord modified to increase fabric substantivity.

The pro-accords of the present invention are useful in personal care and personal hygiene articles including inter alia creams and lotions, make-up, sun tan lotions, balms, salves, depilatory agents all of which may further comprise one or more pharmaceutically active ingredients; hair care articles such as shampoos and mousses and hair sprays; laundry detergent composition which include heavy duty granular and liquid, light duty liquid, laundry bars, pastes and gels; hard surface cleaning compositions. The pro-accords of the present invention are also suitable for use in fine fragrances, colognes, eau de toilettes, after shave lotions and the like wherein slow release of the fragrance raw material is important.

The formulator is not limited by the present invention to delivering the pro-accords of the present invention via a carrier article, that is via laundry compositions, hand cream lotions, etc. The pro-accords of the present invention are suitable for providing an enduring fragrance or fragrance mixture to articles comprised of paper or paper-type materials. Examples include, catamenials, diapers, paper towels, articles for the mediation of incontinence, and the like.

The formulator can formulate a fragrance delivery system which comprises pro-accords which are stable, that is do not begin to break down until triggered by a "catalyst". The catalyst, depending upon the structure of the pro-accord, may be added moisture, a relative shift in pH, or an increase in temperature. For example, if water itself is a suitable catalyst for initiating the release of fragrance raw materials from a pro-accord, a paper towel which has been impregnated with the pro-accords can be moistened and then used to deliver the fragrance to a situs.

In addition, the formulator may use the fragrance delivery system of present invention as a means for indicating that a condition exists. For example, a specific liquid may be stored or shipped in a carton, vessel, or container, which may be prone to damage or slow leakage. The package or outer wrapping of the container may be impregnated with the fragrance delivery system of the present invention and upon contact of the liquid material with the pro-accords then release a fragrance raw material having a low odor threshold thereby alerts the user that the package or container has undergone adulteration.

The following are non-limiting example of compositions wherein the pro-accords of the present invention are suitable for use.

Laundry Detergent Compositions

In its basic form, the present invention relates to laundry detergent compositions which comprise the fragrance delivery system described herein above. For example, a laundry composition comprising:

a) at least about 0.01%, preferably from about 0.01% to about 15%, more preferably from about 0.1% to about 10%, most preferably from about 1% to about 5% by weight, of one or more pro-accords described hereinabove;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant; and c) the balance carriers and adjunct ingredients.

Surfactant systems

The instant cleaning compositions may contain at least about 0.01% by weight of a surfactant selected from the group consisting of anionic, cationic, nonionic, ampholytic and zwitterionic surface active agents. Preferably the solid (i.e. granular) and viscous semi-solid (i.e. gelatinous, pastes, etc.) systems of the present invention, surfactant is preferably present to the extent of from about 0.1% to 60%, more preferably 0.1% to about 30% by weight of the composition.

Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("AE$_x$S"; especially EO 1–7 ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions.

The $C_{10}$–$C_{18}$ N-alkyl polyhydroxy fatty acid amides are highly preferred, especially the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates (AS), such as those illustrated above, have the general formula ROSO3-M+ wherein R is typically a linear C8–22 hydrocarbyl group and M is a water solublizing cation. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure
$CH_3(CH_2)_n(CHOSO_3^-M^+)(CH_2)_mCH_3$
wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. See also U.S. Pat. No. 5,349,101, Lutz et al., issued Sep. 20, 1994; U.S. Pat. No. 5,389,277, Prieto, issued Feb. 14, 1995.

The preferred surfactants of the present invention are anionic surfactants, however, other surfactants useful herein are described below.

The compositions of the present invention can also comprise at least about 0.01%, preferably at least 0.1%, more preferably from about 1% to about 30%, of an nonionic detersive surfactant. Preferred nonionic surfactants such as $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), block alkylene oxide condensate of $C_6$ to $C_{12}$ alkyl phenols, alkylene oxide condensates of $C_8$–$C_{22}$ alkanols and ethylene oxide/propylene oxide block polymers (Pluronic™-BASF Corp.), as well as semi polar nonionics (e.g., amine oxides and phosphine oxides) can be used in the present compositions. An extensive disclosure of these types of surfactants is found in U.S. Pat. No. 3,929,678, Laughlin et al., issued Dec. 30, 1975, incorporated herein by reference.

Alkylpolysaccharides such as disclosed in U.S. Pat. No. 4,565,647 Llenado (incorporated herein by reference) are also preferred nonionic surfactants in the compositions of the invention.

More preferred nonionic surfactants are the polyhydroxy fatty acid amides having the formula:

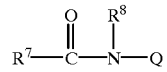

wherein $R^7$ is $C_5$–$C_{31}$ alkyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; $R^8$ is selected from the group consisting of hydrogen, $C_1$–$C_4$ alkyl, $C_1$–$C_4$ hydroxyalkyl, preferably methyl or ethyl, more preferably methyl. Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. Preferred Q is derived from a reducing sugar in a reductive arnination reaction. More preferably Q is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Q. It should be understood that it is by no means intended to exclude other suitable raw materials. Q is more preferably selected from the group consisting of —$CH_2(CHOH)_nCH_2OH$, — $CH(CH_2OH)(CHOH)_{n-1}CH_2OH$, —$CH_2(CHOH)_2$—$(CHOR')(CHOH)CH_2OH$, and alkoxylated derivatives thereof, wherein n is an integer from 3 to 5, inclusive, and R' is hydrogen or a cyclic or aliphatic monosaccharide. Most preferred substituents for the Q moiety are glycityls wherein n is 4, particularly —$CH_2(CHOH)_4CH_2OH$.

$R^7CO$—N< can be, for example, cocamide, stearamide, oleamide, lauramide, myristamide, capricamide, palmitamide, tallowarnide, etc.

$R^8$ can be, for example, methyl, ethyl, propyl, isopropyl, butyl, 2-hydroxy ethyl, or 2-hydroxy propyl.

Q can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

A particularly desirable surfactant of this type for use in the compositions herein is alkyl-N-methyl glucomide, a compound of the above formula wherein $R^7$ is alkyl (preferably $C_{11}$–$C_{17}$), $R^8$, is methyl and Q is 1-deoxyglucityl.

Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used.

Laundry Adjunct Ingredients

The following are non-limiting examples of adjunct ingredients useful in the laundry compositions of the present invention, said adjunct ingredients include builders, optical brighteners, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the NaSKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1}$·$yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$[M_z(zAlO_2)_y]\cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

$$Na_{12}[(AlO_2)_{12}(SiO_2)_{12}]\cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of usefull materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially usefull in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Other Ingredients—A wide variety of other ingredients useful in detergent compositions can be included in the compositions herein, including other active ingredients, carriers, hydrotropes, processing aids, dyes or pigments, solid fillers for bar compositions, etc. Other optional ingredients include enzymes, bleaches, bleach activators, bleach catalysts, photoactivators, dyes, fluorescers, fabric conditioners, hydrolyzable surfactants, optical brighteners, preservatives, anti-oxidants, chelants, stabilizers, anti-shrinkage agents, anti-wrinkle agents, soil release agents, germicides, fungicides, dispersents, and anti corrosion agents. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13\text{-}15}$ ethoxylated alcohol (EO 7) nonionic surfactant. Typically, the enzyme/surfactant solution is 2.5× the weight of silica. The resulting powder is dispersed with stirring in silicone oil (various silicone oil viscosity in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergent compositions.

The detergent compositions herein will preferably be formulated such that, during use in aqueous cleaning operations, the wash water will have a pH of between about 6.5 and about 11, preferably between about 7.5 and 10.5. Laundry products are typically at pH 9–11. Techniques for controlling pH at recommended usage levels include the use of buffers, alkalis, acids, etc., and are well known to those skilled in the art.

The following are non-limiting examples of the fragrance delivery system and the pro-accords which comprise said system.

Hard Surface Cleaning Compositions

The pro-accords of the present invention are useful for delivering a pleasurable scent or fragrance to a hard surface which has been cleaned. The slow release of the fragrance raw material provides for a protracted sense of "freshness".

The hard surface cleaners of the present invention can be in any form inter alia liquid, semi-solid, gelatinous, or solid. The cleaner may be a scouring cleaner and therefore comprise an abrasive material.

Hard surface cleaning compositions according to the present invention having enhanced perfume retention as well as high surface shine and low streaking, comprises:

a) at least about 0.1%, preferably at least 0.5% by weight, of a sulfosuccinamate having the formula:

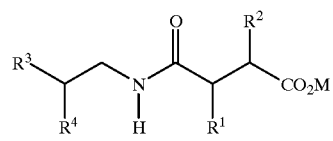

wherein $R^1$ and $R^2$ are hydrogen or —$SO_3M^2$ provided $R^1$ does not equal $R^2$; $R^3$ is butyl when $R^4$ is ethyl and $R^3$ is pentyl when $R^4$ is propyl; M and $M^2$ are independently hydrogen or a salt forming cation;

b) at least about 0.1%, preferably at least 0.5% by weight, of a nonionic surfactant having the formula $CH_3(CH_2)_xCH_2O(CH_2CH_2O)_yH$
wherein x is from about 6 to about 12, y is from about 3.5 to about 10;

c) at least about 0.01%, preferably from about 0.01% to about 15%, more preferably from about 0.1% to about 10%, most preferably from about 0.2% to about 1% by weight, of one or more pro-accords according to the present invention; and d) the balance carriers and adjunct ingredients, said adjunct ingredients selected from the group consisting of abrasives, builders, bleaches, bleach boosters, clays, detersive surfactants, thickeners, dispersents, enzymes, dyes, colorants, filler salts, hydrotropes, enzymes, preservatives, anti-oxidants, chelants, stabilizers, germicides, fungicides, solvents, photodisinfectants, and mixtures thereof.

This example of a preferred hard surface cleaning composition according to the present invention described above comprises either the dianionic surfactant N-2-ethylhexyl sulfosuccinamate, N-2-propylheptyl sulfosuccinamate, or mixtures thereof having the formula:

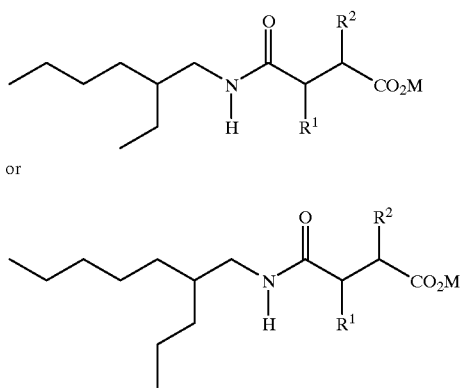

or wherein $R^1$ and $R^2$ are selected from hydrogen or the moiety $-SO_3M^2$, provided however that $R^1$ and $R^2$ are not the same, that is when $R^1$ is hydrogen, $R^2$ must be $SO_3M^2$ and vice versa. M and $M^2$ are independently selected from hydrogen or a salt forming cation. Three carbon atoms in the above molecule are chiral centers, that is they individually have the capacity to form optical isomers or enantiomers. In addition, when two or more of these chiral carbons are taken together they may form diasteriomeric pairs or combinations. For the purposes of the present invention the N-2-ethylhexyl sulfosuccinamate is drawn such that each chiral center is shown in its racemic form. For the purposes of the present invention all isomeric forms of N-2-ethylhexyl sulfosuccinamate are suitable for use in the compositions of the present invention.

M and $M^2$ may be hydrogen or a salt forming cation depending upon the method of synthesis chosen and the pH of the final hard surface cleaner. Examples of salt forming cations are lithium, sodium, potassium, calcium, magnesium, quaternary alkyl amines having the formula

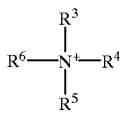

wherein $R^3$, $R^4$, $R^5$ and $R^6$ are independently hydrogen, $C_1$–$C_{22}$ alkylene, $C_4$–$C_{22}$ branched alkylene, $C_1$–$C_6$ alkanol, $C_1$–$C_{22}$ alkenylene, $C_4$–$C_{22}$ branched alkenylene, and mixtures thereof. A different salt forming cation may be chosen for the carboxylate moiety ($-CO_2-$) than is chosen for the sulfonate moiety ($-SO_3-$). Preferred cations are ammonium ($R^3$, $R^4$, $R^5$ and $R^6$ equal hydrogen), sodium, potassium, mono-, di-, and trialkanol ammonium, and mixtures thereof. The monoalkanol ammonium compounds of the present invention have $R^3$ equal to $C_1$–$C_6$ alkanol, $R^4$, $R^5$ and $R^6$ equal to hydrogen; dialkanol ammonium compounds of the present invention have $R^3$ and $R^4$ equal to $C_1$–$C_6$ alkanol, $R^5$ and $R^6$ equal to hydrogen; trialkanol ammonium compounds of the present invention have $R^3$, $R^4$ and $R^5$ equal to $C_1$–$C_6$ alkanol, $R^6$ equal to hydrogen. Preferred alkanol ammonium salts of the present invention are the mono-, di- and tri-quaternary ammonium compounds having the formulas:

$H_3N^+CH_2CH_2OH$, $H_2N^+(CH_2CH_2OH)_2$, $HN^+(CH_2CH_2OH)_3$.

Preferred M and $M^2$ are hydrogen, sodium, potassium and the $C_2$ alkanol ammonium salts listed above; most preferred are hydrogen and sodium.

Nonionic Surfactant

The hard surface cleaning compositions of the present invention preferably further comprises a nonionic surfactant having the formula $CH_3(CH_2)_xCH_2O(CH_2CH_2O)_yH$ wherein x is from about 6 to about 12, preferably from about 8 to about 10; y is from about 3.5 to about 10, preferably from about 4 to about 7. For the purposes of the present invention the index y refers to the average degree of ethoxylation obtained when contacting a suitable alcohol with a source of ethyleneoxy moieties, and therefore represents all fractional parts within the range 3.5 to 10.

Other preferred hard surface cleaning compositions include solid scouring powders having abrasives such as perlite or sodium carbonate, foam cleaners, and liquids wherein the carrier material may comprise liquids other than water.

Fragrance Delivery System

In its most basic form the fragrance delivery system of the present invention comprises one or more pro-accords, preferably admixed with a suitable carrier or vehicle for delivery of the pro-accord or pro-accord admixture to a situs. The delivery of an enduring fragrance to a situs can be accomplished by formulating a composition comprising:

a) at least about 0.01%, preferably from about 0.01% to about 15%, more preferably from about 0.1% to about 5%, most preferably from about 0.2% to about 1% by weight, of one or more β-ketoesters according to the present invention; and b) the balance comprising a carrier, said carrier selected from the group consisting of water, $C_1$–$C_3$ alcohols, $C_2$–$C_8$ poly hydroxy alcohols, water soluble cationic and anionic polymers, polyethylene glycols, and mixtures thereof; and by applying said composition to the situs. For example, the formulation may be sprayed directly onto clothing which are in need of "refreshening", into the air of a room, or applied to the fabric of an article of furniture.

Example of suitable carriers include inter alia water, methanol, ethanol, isopropanol, and propylene glycol. In addition, water-soluble polymers, e.g., water-soluble cationic polymer and water-soluble anionic polymers can be used in the composition of the present invention to provide additional fragrance delivery benefits.

a. Cationic polymers, e.g., polyamines

Water-soluble cationic polymers, e.g., those containing amino functionalities, amido functionalities, and mixtures thereof, are useful in the present invention to control certain acid-type odors and therefore enhance the perception of the fragrance raw materials which are released by the pro-accords of the present invention.

b. Anionic polymers, e.g., polyacrylic acid

Likewise, water-soluble anionic polymers, e.g., polyacrylic acids and their water-soluble salts are useful in the present invention to control certain amine-type odors which may be present at the situs where the pro-accords are delivered. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

The following are non-limiting examples of the β-ketoester pro-accords of the present invention and the use thereof.

EXAMPLE 1

Preparation of 3,7-dimethyl-1,6-octadien-3-3-(β-naphthyl)-3-oxo-propionate

Lithium diisopropylamide (101.0 mL of a 2.0 M solution, 0.202 mol) is placed into a 500 mL three-necked round-bottomed flask fitted with a magnetic stirrer, internal thermometer, argon inlet, and addition funnel. The flask is placed in a dry ice-acetone bath. 3,7-Dimethyl-1,6-octadien-3-yl acetate (linalyl acetate) in the amount of (18.66 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.43 g, 0.090 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and GC analysis and the structure confirmed by mass spectrometry, $^1$H and $^{13}$C NMR.

EXAMPLE 2

Preparation of 2,6-dimethyl-7-octen-2-yl 3-(4-methoxyphenyl)-3-oxo-propionate

N-Isopropylcyclohexylamine (25.00 g, 0.177 mol) and THF in the amount of 200 mL is placed into a 1000 mL three-necked round-bottomed flask fitted with a magnetic stirrer, internal thermometer, argon inlet, and addition funnel. The flask is placed in a ice-methanol bath cooled to −5° C. and its contents treated with n-butyllithium in the amount of (70.8 mL of a 2.50 M solution, 0.177 mol). The mixture is stirred for 20 min and then cooled to −78° C. 2,6-Dimethyl-7-octen-2-yl acetate (dihydromyrcenyl acetate) in the amount of (17.55 g, 0.089 mol) is dissolved in THF (10 mL) and the resulting solution added to the flask over 45 min. Once addition is complete, the mixture is stirred for an additional 15 min before being treated with a solution of p-methoxybenzoyl chloride in the amount of (15.10 g, 0.090 mol) dissolved in THF (25 ml) over 30 min and then stirred for 1 h. The mixture is warmed to 0° C. and then treated with 90 mL of 20% HCl an hour later. The mixture is poured into a separatory funnel containing ether (100 ml) and water (200 ml). The aqueous layer is extracted with ether (100 ml). The combined organic layers are washed with saturated NaHCO$_3$ solution (2×100 ml), water (2×100 ml) and brine (100 ml), dried over MgSO$_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and the structure confirmed by $^1$H and $^{13}$C NMR.

EXAMPLE 3

Preparation of 2,6-dimethyl-7-octen-2-yl 3-(4-nitrophenyl)-3-oxo-propionate

Lithium diisopropylamide (121.0 mL of a 2.0 M solution, 0.243 mol) is placed into a 500 mL three-necked round-bottomed flask fitted with a magnetic stirrer, internal thermometer, argon inlet, and addition funnel. The flask is placed in a dry ice-acetone bath. 2,6-Dimethyl-7-octen-2-yl acetate (22.66 g, 0.114 mol) is dissolved in THF (5 mL) and the resulting solution added to the flask over 45 min. Once addition is complete, the mixture is stirred for an additional 15 min. before being treated with a solution of 4-nitrobenzoyl chloride (20.00 g, 0.108 mol) dissolved in THF (25 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 4

Preparation of 2,6-dimethyl-7-octen-2-yl 3-(β-naphthyl)-3-oxo-propionate

Lithium diisopropylamide in the amount of (100.0 mL of a 2.0 M solution, 0.201 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate in the amount of (18.75 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.00 g, 0.089 mol) dissolved in THF (25 mL) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate dissolved in petroleum ether) to give an oil. Purity of the product is determined by thin layer chromatography and the structure confirmed by $^1$H and $^{13}$C NMR.

EXAMPLE 5

Preparation of 3,7-dimethyl-1,6-octadien-3-yl 3-(4-methoxyphenyl)-3-oxo-propionate Lithium diisopropylamide (119.0 mL of a 2.0 M solution, 0.238 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (22.04 g, 0.112 mol) is dissolved in THF (5 mL) and the resulting solution added to the flask over 45 min. Once addition is complete, the mixture is stirred for an additional 15 min. before being treated with a solution of p-anisoyl chloride (35.00 g, 0.106 mol) dissolved in THF (30 mL) over 30 min. The mixture is warmed to −20° C. and stirred at that temperature for 18 h. After warming to 0° C., the mixture is quenched with 20% HCl (80 mL). The mixture is poured into a separatory funnel containing ether (150 mL) and water (250 mL). The aqueous layer is extracted with ether (150 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an oil. The oil is purified by column chromatography (elution with 2% ethyl acetate/petroleum ether) to yield a colorless oil having $^1$H and $^{13}$C NMR spectra consistent with the desired product.

EXAMPLE 6

Preparation of (α,α-4-trimethyl-3-cyclohexenyl) methyl 3-(β-naphthyl)-3-oxo-propionate Lithium diisopropylamide (171.0 mL of a 2.0 M solution, 0.342 mol) is placed into a 1000 mL three-necked round-bottomed flask fitted with a magnetic stirrer, internal thermometer, argon inlet, and addition funnel. The flask is cooled to −78° C. (α,α-4-Trimethyl-3-cyclohexenyl)methyl acetate (30.00 g, 0.153 mol) is dissolved in THF (10 mL) and the resulting solution added to the flask over 45 min. Once addition is complete, the mixture is stirred for an additional 15 min. before being treated with a solution of 2-naphthoyl chloride (29.00 g, 0.152 mol) dissolved in THF (50 mL) over 30 min. The mixture is warmed to −20° C. and stirred at that temperature for 18 h. After warming to 0° C., the mixture is quenched with 20% HCl (105 mL). The mixture is poured into a separatory funnel containing ether (150 mL) and water (250 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an oil. The oil is purified by column chromatography (elution with 2% ethyl acetate/petroleum ether) to yield a semi-white solid which is triturated in cold n-pentane to yield a white powder having $^1$H and $^{13}$C NMR spectra consistent with the desired product.

EXAMPLE 7

Preparation of 3,7-dimethyl-1,6-octadien-3-yl 3-(α-naphthyl)-3-oxo-propionate

Lithium diisopropylamide (96.3 mL of a 2.0 M solution, 0.193 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (17.81 g, 0.091 mol) is dissolved in THF (5 mL) and the resulting solution added to the flask over 45 min. Once addition is complete, the mixture is stirred for an additional 15 min. before being treated with a solution of 1-naphthoyl chloride (16.82 g, 0.086 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an oil. The oil is purified by column chromatography (elution with 2% ethyl acetate/petroleum ether) to yield a colorless oil having $^1$H and $^{13}$C NMR spectra consistent with the desired product.

EXAMPLE 8

Preparation of cis 3-hexen-1-yl 3-(β-naphthyl)-3-oxo-propionate

Lithium diisopropylamide (133.0 mL of a 2.0 M solution, 0.266 mol) is placed into a 500 mL three-necked round-bottomed flask fitted with a magnetic stirrer, internal thermometer, argon inlet, and addition funnel. The flask is cooled to −78° C. cis 3-Hexenyl acetate (17.80 g, 0.125 mol) is dissolved in THF (10 mL) and the resulting solution added to the flask over 45 min. Once addition is complete, the mixture is stirred for an additional 15 min. before being treated with a solution of 2-naphthoyl chloride (22.51 g, 0.118 mol) dissolved in THF (30 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 9

Preparation of 9-decen-1-yl 3-(β-naphthyl)-3-oxo-propionate

Lithium diisopropylamide (79.8 mL of a 2.0 M solution, 0.160 mol) is placed into a 250 mL three-necked round-bottomed flask fitted with a magnetic stirrer, internal thermometer, argon inlet, and addition funnel. The flask is cooled to −78° C. 9-Decen-1-yl acetate (14.91 g, 0.075 mol) is dissolved in THF (5 mL) and the resulting solution added to the flask over 45 min. Once addition is complete, the mixture is stirred for an additional 15 min. before being treated with a solution of 2-naphthoyl chloride (13.80 g, 0.071 mol) dissolved in THF (25 mL) over 30 min. The mixture is warmed to −20° C. and stirred at that temperature for 18 h. After warming to 0° C., the mixture is quenched with 20% HCl (47 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 10

Preparation of 3,7-dimethyl-1,6-octadien-3-yl 3-(nonanyl)-3-oxo-propionate

Lithium diisopropylamide (133.7 mL of a 2.0 M solution, 0.267 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (24.73 g, 0.126 mol) is dissolved in THF (40 mL) and the resulting solution added to the flask over 45 min. Once addition is complete, the mixture is stirred for an additional 15 min. before being treated with a solution of nonanoyl chloride (21.88 g, 0.119 mol) over 30 min. The mixture is warmed to −20° C. and stirred at that temperature for 18 h. After warming to 0° C., the mixture is quenched with 20% HCl (60 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 11

Preparation of 2,6-dimethyl-7-octen-2-yl 3-(nonanyl)-3-oxo-propionate

Lithium diisopropylamide (75.7 mL of a 2.0 M solution, 0.151 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate (14.14 g, 0.071 mol) is dissolved in THF (20 mL) and the resulting solution added to the flask over 45 min. Once addition is complete, the mixture is stirred for an additional 15 min. before being treated with a solution of nonanoyl chloride (12.38 g, 0.067 mol) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 12

Preparation of 3,7-dimethyl-1,6-octadien-3-yl 3-oxo-butyrate

A mixture of linalool (100 g, 0.648 mol) and 4-dimethylaminopyridine (0.40 g, 3.20 mmol) in a 500 mL three-necked round-bottomed flask fitted with a condenser, argon inlet, addition funnel, magnetic stirrer and internal thermometer is heated to 55° C. Diketene (54.50 g, 0.648 mol) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromtography (elution with dichloromethane) yields the desired product in 92% yield and nearly colorless.

EXAMPLE 13

Preparation of 2,6-dimethyl-7-octen-2-yl 3-oxo-butyrate

A mixture of dihydromyrcenol (37.88 g, 0.240 mol) and 4-dimethylaminopyridine (0.16 g, 1.30 mmol) in a 100 mL three-necked round-bottomed flask fitted with a condenser, argon inlet, addition funnel, magnetic stirrer and internal thermometer is heated to 50–60° C. Diketene (20.16 g, 0.240 mol) is added dropwise in the course of 15 min. The mixture has a slight exotherm and turned from yellow to red during this time. After stirring an additional hour at 50° C., the mixture is cooled to room temperature. At this point, NMR analysis indicates the reaction is complete. Purification of the product mixture by flash chromatography (elution with dichloromethane) yields the desired product in 95% yield as a nearly colorless oil.

EXAMPLE 14

Preparation of 3,7-dimethyl-1,6-octadien-3-yl 3-(β-naphthyl)-3-oxo-propionate

Crude 3,7-dimethyl-1,6-octadien-3-yl 3-oxo-butyrate (154.51, 0.648 mol) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to ~1 with 20% HCl. The mixture is transferred to a separatory funnel containing diethyl ether (500 mL) and water (500 mL). The layers are separated and the organic phase is washed with saturated NaHCO$_3$ solution (2×500 mL), dried over MgSO$_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoyl)acetate. A portion of this material is purified by column chromatography (elution with 2.5% ethyl acetate in hexanes) to give the desired product as a light yellow oil.

EXAMPLE 15

Preparation of 3,7-dimethyl-1,6-octadien-3-yl 3-(β-naphthyl)-3-oxo-2,2-dimethylpropionate Sodium hydride (2.30 g, 0.057 mol, 60%) and tetrahydrofuran (50 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (8.94 g, 0.025 mol) dissolved in 50 mL of tetrahydrofuran is added dropwise to the flask over 30 min. During addition, the mixture evolves gas. After stirring for 1 h, methyl iodide (7.24 g, 0.051 mol) is added to the reaction mixture. Stirring continues for 2 h at 0° C. and then at room temperature for 18 h. The mixture is neutralized with 20% HCl and extracted with diethyl ether. The organic layers are washed with saturated NaHCO$_3$ solution, water, dried over MgSO$_4$, filtered, concentrated by rotary evaporation and purified by flash chromatography to yield the desired compound. Structure is confirmed my $^1$H and $^{13}$C NMR.

EXAMPLE 16

Preparation of 3,7-dimethyl-1,6-octadien-3-yl 3-(β-naphthyl)-3-oxo-2-methylpropionate Sodium hydride (3.92 g, 0.098 mol, 60%) and tetrahydrofuran (100 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (15.28 g, 0.044 mol) dissolved in 50 mL of tetrahydrofuran is added dropwise to the flask over 30 min. During addition, the mixture evolves gas. After stirring for 1 h, methyl iodide (10.65 g, 0.075 mol) is added to the reaction mixture. Stirring continues for 2 h at 0° C. and then at room temperature for 18 h. The mixture is neutralized with 20% HCl and extracted with diethyl ether. The organic layers are washed with saturated NaHCO$_3$ solution, water, dried over MgSO$_4$, filtered, concentrated by rotary evaporation and purified by flash chromatography to yield the desired compound. Structure is confirmed my $^1$H and $^{13}$C NMR.

EXAMPLE 17

Preparation of 3,7-dimethyl-1,6-octadien-3-yl 3-(hexyl)-3-oxo-propionate 3,7-Dimethyl-1,6-octadien-3-yl 3-oxo-butyrate (30.00 g, 0.126 mol), dichloromethane (50 mL) and methyl ethyl ketone (10 mL) are combined in a 500 mL three-necked round-bottomed flask fitted with an internal thermometer, addition funnel, condenser and argon inlet. Calcium hydroxide (9.80 g, 0.132 mol, powdered) is added to the flask and the slurry stirs for 1 h. Heptanoyl chloride (17.84 g, 0.120 mol) in 10 ml of dichloromethane is added over 15 min so as to keep the reaction temperature between 35–40° C. The reaction continues to stir at 35–40° C. for 2 h. Ammonium chloride (7.06 g, 0.132 mol) dissolved in 20 mL of water is added to the flask. After 20 min, concentrated ammonium hydroxide is added to the mixture to adjust the pH to ~9.0. After 1 h, 20% HCl solution is added to drop the pH to ~1.0. After 1 h, the mixture is poured into 300 mL of dichloromethane. The layers are separated and the aqueous phase extracted with 100 mL of dichloromethane. The combine organic layers are washed with saturated NaHCO$_3$ solution, water, dried over MgSO$_4$, filtered, concentrated by rotary evaporation and purified by flash chromatography to yield the desired compound. Structure is confirmed my $^1$H and $^{13}$C NMR.

EXAMPLE 18

Preparation of 3,7-dimethyl-1,6-octadien-3-yl 3-oxo-2-benzylbutyrate

Potassium carbonate (3.92 g, 0.028 mol), 3,7-dimethyl-1,6-octadien-3-yl 3-oxo-butyrate (4.80 g, 0.030 mol), benzyl chloride (4.80 g, 0.038 mol) and acetone (15 mL) are placed in a 50 mL round-bottomed flask fitted with a magnetic stirrer, condenser and argon inlet. The mixture is heated to reflux for 18 h. The cooled mixture is filtered and concentrated by rotary evaporation. The resulting oil is purified on silica gel to yield the desired compound. Structure is confirmed by thin layer chromatography and $^1$H and $^{13}$C NMR.

Other methods for preparing β-ketoesters can be found in U.S. Pat. No. 5,194,671 Meier issued Mar. 16, 1993 included herein by reference.

The following are examples of a granular laundry detergent composition comprising the fragrance delivery system of the present invention.

TABLE I

| | weight % | | | |
|---|---|---|---|---|
| Ingredient | 19 | 20 | 21 | 22 |
| Sodium C$_{11}$-C$_{13}$ alkylbenzenesulfonate | 13.3 | 13.7 | 10.4 | 11.1 |
| Sodium C$_{14}$-C$_{15}$ alcohol sulfate | 3.9 | 4.0 | 4.5 | 11.2 |
| Sodium C$_{14}$-C$_{15}$ alcohol ethoxylate (0.5) sulfate | 2.0 | 2.0 | 0.0 | 0.0 |
| Sodium C$_{14}$-C$_{15}$ alcohol ethoxylate (6.5) | 0.5 | 0.5 | 0.5 | 1.0 |
| Tallow fatty acid | 0.0 | 0.0 | 0.0 | 1.1 |
| Sodium tripolyphosphate | 0.0 | 41.0 | 0.0 | 0.0 |
| Zeolite A, hydrate (0.1–10 micron size) | 26.3 | 0.0 | 21.3 | 28.0 |
| Sodium carbonate | 23.9 | 12.4 | 25.2 | 16.1 |
| Sodium Polyacrylate (45%) | 3.4 | 0.0 | 2.7 | 3.4 |
| Sodium silicate (1:6 ratio NaO/SiO$_2$)(46%) | 2.4 | 6.4 | 2.1 | 2.6 |
| Sodium sulfate | 10.5 | 10.9 | 8.2 | 15.0 |
| Sodium perborate | 1.0 | 1.0 | 5.0 | 0.0 |
| Poly(ethyleneglycol), MW ~4000 (50%) | 1.7 | 0.4 | 1.0 | 1.1 |
| Citric acid | 0.0 | 0.0 | 3.0 | 0.0 |
| Nonyl ester of sodium p-hydroxybenzenesulfonate | 0.0 | 0.0 | 5.9 | 0.0 |
| Soil release polymer[1] | 1.5 | 1.5 | 1.5 | 1.5 |
| Pro-accord[2] | 1.0 | 1.5 | 0.0 | 0.0 |

TABLE I-continued

| Ingredient | weight % | | | |
|---|---|---|---|---|
| | 19 | 20 | 21 | 22 |
| Pro-accord[3] | 0.0 | 0.0 | 2.5 | 1.5 |
| Minors[4] | 7.0 | 2.1 | 4.1 | 6.3 |

[1]Soil release polymer according to U.S. Pat. 4,968,451, Scheibel et al., issued November 6, 1990.
[2]Pro-accord according to Example 1.
[3]Pro-accord according to Example 2.
[4]Balance to 100% can, for example, include minors like optical brightener, perfume, suds suppresser, soil dispersant, protease, lipase, cellulase, chelating agents, dye transfer inhibiting agents, additional water, and fillers, including $CaCO_3$, talc, silicates, etc.

The following are examples of liquid laundry detergent compositions which comprise the fragrance delivery system of the present invention.

TABLE II

| Ingredients | Weight % | | | | |
|---|---|---|---|---|---|
| | 23 | 24 | 25 | 26 | 27 |
| Polyhydroxy coco-fatty acid amide | 3.50 | 3.50 | 3.15 | 3.50 | 3.00 |
| NEODOL 23-9[1] | 2.00 | 0.60 | 2.00 | 0.60 | 0.60 |
| $C_{25}$ Alkyl ethoxylate sulphate | 19.00 | 19.40 | 19.00 | 17.40 | 14.00 |
| $C_{25}$ Alkyl sulfate | — | — | — | 2.85 | 2.30 |
| $C_{10}$-Aminopropylamide | — | — | — | 0.75 | 0.50 |
| Citric acid | 3.00 | 3.00 | 3.00 | 3.00 | 3.00 |
| Tallow fatty acid | 2.00 | 2.00 | 2.00 | 2.00 | 2.00 |
| Ethanol | 3.41 | 3.47 | 3.34 | 3.59 | 2.93 |
| Propanediol | 6.22 | 6.35 | 6.21 | 6.56 | 5.75 |
| Monomethanol amine | 1.00 | 0.50 | 0.50 | 0.50 | 0.50 |
| Sodium hydroxide | 3.05 | 2.40 | 2.40 | 2.40 | 2.40 |
| Sodium p-toluene sulfonate | 2.50 | 2.25 | 2.25 | 2.25 | 2.25 |
| Borax | 2.50 | 2.50 | 2.50 | 2.50 | 2.50 |
| Protease[2] | 0.88 | 0.88 | 0.88 | 0.88 | 0.88 |
| Lipolase[3] | 0.04 | 0.12 | 0.12 | 0.12 | 0.12 |
| Duramyl[4] | 0.10 | 0.10 | 0.10 | 0.10 | 0.40 |
| CAREZYME | 0.053 | 0.053 | 0.053 | 0.053 | 0.053 |
| Optical Brightener | 0.15 | 0.15 | 0.15 | 0.15 | 0.15 |
| Pro-accord[5] | 1.18 | 1.18 | 1.18 | 1.18 | 1.75 |
| Soil release agent[6] | 0.22 | 0.15 | 0.15 | 0.15 | 0.15 |
| Fumed silica | 0.119 | 0.119 | 0.119 | 0.119 | 0.119 |
| Minors, aesthetics, water | balance | balance | balance | balance | balance |

[1]$C_{12}$-$C_{13}$ alkyl E9 ethoxylate as sold by Shell Oil Co.
[2]Bacillus amyloliquefaciens subtilisin as described in WO 95/10615 published April 20, 1995 by Genencor International.
[3]Derived from Humicola lanuginosa and commercially available from Novo.
[4]Disclosed in WO 9510603 A and available from Novo.
[5]Pro-accord according to Example 3.
[6]Terephthalate co-polymer as disclosed in U.S. Pat. 4,968,451, Scheibel et al., issued November 6, 1990.

EXAMPLE 28

The following is an example of a solid bleaching composition which comprises a pro-accord according to the present invention.

TABLE III

| Ingredients | weight % |
|---|---|
| Nonanoyloxybenzene sulfonate | 7.0 |
| Sodium perborate | 20.0 |
| DTPA[1] | 10.0 |
| Citric acid (coated) | 20.0 |

TABLE III-continued

| Ingredients | weight % |
|---|---|
| Fragrance[2] | 1.0 |
| Pro-fragrance[3] | 2.0 |
| Sodium sulfate | balance |

[1]Diethylenetriamine pentaacetic acid.
[2]Dihydromycenol.
[3]Pro-accord according to Example 7.

EXAMPLE 29

The following is an example of a liquid bleaching composition comprising a pro-accord of the present invention.

TABLE IV

| Ingredients | weight % |
|---|---|
| Sodium hypochlorite | 5.25 |
| $C_{12}$ Dimethylamine oxide | 0.9 |
| Optical brightener[1] | 0.3 |
| Fragrance[2] | 1.0 |
| Pro-accord[3] | 2.0 |
| Sodium hydroxide | 1.0 |
| Water | balance |

[1]4,4-bis(4-phenyl-2-H-1,2,3-triazolyl)-(2)-stilbene-2,2-disulfonic acid dipotassium salt.
[2]A mixture of linalool (20%), tetrahydrolinalool (30%), Galaxolide (30%), and citral dimethylacetal (20%).
[3]Pro-accord according to Example 3.

Skin Conditioning Lotions

An example of a skin care composition of the present invention comprises an ester having a total number of carbon atoms in excess of about 28, for example lauryl laurate, lauryl myristate, myristyl myristate, behenyl caprate, cetearyl palmitate, behenyl stearate, more preferably cetearyl palmitate and cetyl stearate.

The present compositions in addition to the esters described herein above, contain an emollient material in an amount such that the amount of ester plus emollient is from about 0.2% to about 25% of the total composition, preferably from about 4% to about 18%. One function of the emollient is to ensure that the ester is plasticized sufficiently to allow it to be in a film-like state on the skin. The emollient in the present compositions is selected from the group consisting of fatty alcohols, esters having fewer than about 24 total carbon atoms (e.g. isopropyl palmitate), branched chain esters having greater than about 24 total carbon atoms (e.g. cetearyl octonate), squalane, liquid or solid paraffins, mixtures of fatty acids and squalane, mixtures of fatty acids and liquid or solid paraffins and mixtures thereof. The aforementioned esters, those having fewer than. 24 carbon atoms or branched and having more than 24 carbon atoms, if used as an emollient should preferably be used in an mount equal to about a third of the long chain ester. The particular emollient selected depends in part on the particular ester selected since proper plasticization, as indicated above, is desired. The emollient for the esters having more than 28 carbon atoms is preferably selected from the group consisting of squalane, liquid or solid paraffins and mixtures of fatty alcohols with squalane or paraffins. Typical fatty alcohols and fatty acids useful in the present compositions include those having from 12–22 carbon atoms such as cetyl alcohol, myristyl alcohol, stearyl alcohol, stearic acid and palmitic acid. Paraffins include, for example, mineral oil, petrolatum and paraffin wax. It is preferred that distilled water be used in the present compositions.

Optional Components
Oil Phase Components

In addition to the long chain esters, emollients and emulsifiers described previously, the oil phase of the present compositions may contain a variety of materials including:

(a) Esters not meeting the requirements for the long chain ester and not present as an emollient, supra, such as oleyl oleate, isostearyl isostearate, isopropyl lanolate, isopropyl myristate, butyl stearate, myristyl lactate and 2-ethyl hexyl palmitate;

(b) Oils such as castor oil, jojoba oil, cottonseed oil, peanut oil and sesame oil;

(c) Waxes such as ceresin wax, carnuba wax, beeswax and castor wax;

(d) Lanolin, its derivatives and components such as acetylated lanolin, lanolin alcohols and lanolin fatty acids. Lanolin fatty acids are described in U.S. Pat. No. Re. 29,814, Oct. 24, 1978 to W. E. Snyder incorporated herein by reference.

(e) Polyalkylenes such as hydrogenated polyisobutene and polyethylene; and (f) Sterols such as cholesterol and phytosterol.

These optional oil phase materials may comprise up to about 80% of the oil phase, preferably up to about 35%. When used at these levels, the optional components do not impair the occlusive nature of the compositions and add to the composition's total cosmetic performance.

Water Phase Components

The water phase of the compositions may contain many different materials including:

(a) Humectants, such as sorbitol, glycerine, propylene glycol, alkoxylated glucose and hexanetriol at a level of from about 1% to about 20%.

(b) Thickening agents such as carboxyvinyl polymers, ethyl cellulose, polyvinyl alcohol, carboxymethyl cellulose, vegetable gums and clays such as Veegum-.RTM. (magnesium aluminum silicate, R. T. Vanderbilt, Inc.) at a level of from about 0.01% to about 6%;

(c) Proteins and polypeptides at a level of from about 0.1% to about 3%;

(d) Preservatives such as the methyl, ethyl, propyl and butyl esters of hydroxybenzoic acid (Parabens-Mallinckrodt Chemical Corporation) EDTA and imidazolidinyl urea (Germall 115-Sutton Laboratories) at a level of from about 0.2% to about 2.5%; and (e) An alkaline agent such as sodium hydroxide to neutralize, if desired, part of the fatty acids or thickener which may be present.

All of the percentages of these additional water phase components are of the total composition.

The present compositions may also contain agents suitable for aesthetic purposes such as dyes. The compositions of the present invention are preferably substantially free of materials which adversely affect their performance. Therefore, such things as polyethylene glycols are preferably present only at levels below about 1% of the total composition. The pH of the present compositions is preferably in the range of about 7.5–10.

Method of Manufacture

The compositions of the present invention generally have a lotion consistency and may be in the form of oil-in-water or water-in-oil emulsions with the former being preferred because of their more pleasing cosmetic properties. The compositions of the present invention are preferably made by the method comprising the steps of;

a) preparing the oil phase;

b) preparing the water phase; and c) adding the oil phase to the water phase.

Step (a) is carried out by heating the oil phase materials to a temperature of about 75° C. to about 100° C. Step (b) is carried out by heating the water phase materials to a temperature about the same as that of the oil phase. The emulsion is formed by slowly adding the oil phase prepared in step (a) to the water phase prepared in step (b) with stirring. The pro-accords which comprise the fragrance delivery system or other ingredients may be added to the phase in which they are soluble prior to the mixing of the two phases or added directly to the mixed water and oil phases.

In addition to the fragrance-containing compositions for use on human skin, the pro-accords of the present invention are also suitable for use in any odor controlling or fragrance mediating application. A example of this odor control capacity is animal litter and odor control articles useful in lining the cages, stalls, and other living areas of domesticated animals. For example, U.S. Pat. No. 5,339,769 Toth et al., issued Aug. 23, 1994 describes a process for making an absorbent composition which can well accommodate the pro-accord materials of the present invention.

An example of a suitable litter material which comprises the pro-accords of the present invention can be formed by the following process.

A Glatt fluid bed granulator is charged with 1,0000 g of bentonite clay (90% of the particles being greater than 420 microns) and 10 g of a cellulose ether (Methocel™ K1SM Premium, a cellulose ether having a viscosity of 15,000 centipoise (cps) as a 2% aqueous solution). The granulator is started an the product temperature is brought up to about 40° C. (outlet temperature). When the outlet temperature reaches about 40° C., atomized water is sprayed onto the moving powders within the granulator, During the granulation process, inlet air temperature is maintained at 70° C. to 80° C.; air atomization pressure is 28–35 psi; and the spraying cycle is for 45 seconds with a 15 second shaking time.

The clay/cellulose ether agglomerates swell over time. The water hydrates the cellulose ether polymer which produces adhesion to form the granule. At this time it is more advantageous to introduce the pro-accord materials and other aesthetic fragrances. The formation of the granule promotes aggregation of the small sized particles of the inert substrate, e.g. clay particles of about 50 to 600 microns. The formation of a granule significantly reduces the quality of dust in the final product while the litter forms an agglomerate when wetted.

In an alternative embodiment of the clay-based litter box articles/pro-accord admixture, once the clay particles have been formed, a concentrated solution, or an carrier alcohol-based admixture of the pro-accords may be delivered to the surface of the granule by a suitable means.

A deodorant gel stick of the present invention having the composition given below, and being essentially free of water, is prepared as follows.

TABLE V

| Ingredients | Weight % | | |
|---|---|---|---|
| | 39 | 31 | 32 |
| Dipropylene glycol | 39.85 | 51.95 | 75.10 |
| Sodium Stearate | 5.50 | 5.50 | 5.50 |

TABLE V-continued

| Ingredients | Weight % | | |
|---|---|---|---|
| | 39 | 31 | 32 |
| PPG-3 myristyl ether | 29.40 | 25.33 | 15.00 |
| Cyclomethicone-D5 | 21.00 | 13.33 | — |
| Ethanol (absolute; 200 proof) | 1.80 | 1.44 | 1.95 |
| Zinc pyrithione[1] | 0.05 | 0.05 | 0.05 |
| Pro-accord[2] | 2.40 | 2.40 | 2.40 |

[1]Powder form commercially available from Olin.
[2]Pro-accord admixture comprising 75% of the pro-accord from Example 3 and 25% of the pro-accord from Example 6.

All of the above materials, except the fragrance pro-accord, are vigorously mixed and heated to about 121° C. until the mixture is clear. The mixture is them cooled to about 80° C. and the pro-accord is added with stirring. The mixture is poured into stick molds and cooled to room temperature forming the deodorant gel stick compositions of the present invention.

A personal cleanser composition is prepared by combining the following ingredients using conventional mixing techniques.

TABLE VI

| Ingredients | Weight % | | | |
|---|---|---|---|---|
| | 33 | 34 | 35 | 36 |
| Phase A | | | | |
| Water | QS 100 | QS 100 | QS 100 | QS 100 |
| Disodium EDTA | 0.100 | 0.100 | 0.100 | 0.100 |
| Glycerin | 4.00 | 4.00 | 4.00 | 4.00 |
| Methylparaben | 0.200 | 0.200 | 0.200 | 0.200 |
| $C_{10}$–$C_{30}$ alkyl acrylate crosspolymer[1] | 0.150 | 0.150 | 0.150 | 0.150 |
| Carbomer 954[2] | 0.250 | 0.250 | 0.250 | 0.250 |
| Phase B | | | | |
| Stearic Acid | 0.110 | 0.110 | 0.110 | 0.110 |
| Stearyl alcohol | 0.875 | 0.875 | 0.875 | 0.875 |
| Cetyl alcohol | 0.875 | 0.875 | 0.875 | 0.875 |
| Propylparaben | 0.150 | 0.150 | 0.150 | 0.150 |
| Steareth-2 | — | 0.25 | 0.25 | 0.25 |
| Steareth-21 | — | 0.50 | 0.50 | 0.50 |
| Phase C | | | | |
| Sodium hydroxide[3] | 0.130 | 0.130 | 0.130 | 0.130 |
| Phase D | | | | |
| Diisopropyl sebacate | 1.50 | 1.50 | 1.50 | 1.50 |
| Isohexadecane | 5.00 | 2.00 | 5.00 | 5.00 |
| Mineral Oil[4] | — | 5.00 | — | — |
| Phase E | | | | |
| Phenoxyethanol | 0.5 | 0.5 | — | 0.5 |
| Pro-accord[5] | 1.5 | 1.5 | — | — |
| Pro-accord[6] | — | — | 2.20 | 1.5 |
| Phase F | | | | |
| Glucose amide | 0.96 | 0.96 | 0.96 | 0.96 |

[1]Available as Pemulen ® from B. F. Goodrich Corporation.
[2]Available as Carbomer ® 954 from B. F. Goodrich Corporation.
[3]As a 50% aqueous solution.
[4]Light mineral oil available as Drakeol 5 from Penreco, Dickenson, Tx.
[5]Pro-accord according to Example 3.
[6]Pro-accord according to Example 11.

The above Examples 33–36 can be suitably prepared as follows. In a suitable vessel, the Phase A ingredients are mixed at room temperature to form a dispersion and heated with stirring to 70–80° C. In a separate vessel, the Phase B ingredients are heated with stirring to 70–80° C. Phase B is then added to Phase A with mixing to form the emulsion. Next, Phase C is added to neutralize the composition. The Phase D ingredients are added with mixing, followed by cooling to 45–50° C. The Phase E ingredients are then added with stirring, followed by cooling to 40° C. Phase F is heated with mixing to 40° C. and added to the emulsion, which is cooled to room temperature. The resulting cleansing composition is useful for cleansing the skin. The emulsion de-emulsifies upon contact with the skin.

The following non-limiting examples illustrate the hard surface cleaners comprising the fragrance delivery system of the invention.

| Ingredients | Weight % | | | |
|---|---|---|---|---|
| | 37 | 38 | 39 | 40 |
| N-2-ethylhexyl sulfosuccinamate | 3.0 | 3.0 | 3.0 | 3.0 |
| $C_{11}EO_5$ | 7.0 | 14.0 | 14.0 | — |
| $C_{11}EO_7$ | — | — | — | 7.0 |
| $C_{10}EO_7$ | 7.0 | — | — | 7.0 |
| Trisodium citrate | 1.0 | 1.0 | — | 1.0 |
| Potassium carbonate | 0.2 | 0.2 | 0.2 | 0.2 |
| Triethanol amine | — | — | 1.0 | — |
| Polycarboxylate co-polymer[1] | — | — | 0.25 | — |
| Pro-fragrance[2] | 1.0 | 1.0 | 1.0 | 1.0 |
| Alkalinity adjusted to pH | 10.5 | 10.5 | 7.4 | 10.5 |
| Water, salts, fillers | balance | balance | balance | balance |

[1]SOKALAN CP-9.
[2]Pro-accord according to Example 3.

TABLE VIII

| Ingredients | Weight % | | | | | |
|---|---|---|---|---|---|---|
| | 41 | 42 | 43 | 44 | 45 | 46 |
| Surfactant | 0.25 | 3.5 | 5.5 | 6.5 | 6.1 | 9.5 |
| Hypochlorite | 0.9 | 1.4 | 1.4 | 0.5 | 0.5 | 0.5 |
| Phosphate | 6.0 | — | — | — | 13.0 | — |
| Sodium silicate | — | 0.04 | 0.05 | — | 0.5 | — |
| Sodium halide | — | 0.01 | 1.5 | 0.3 | — | 1.1 |
| Calcium carbonate | — | — | — | — | 39.0 | 1.1 |
| Calcium oxide | — | — | — | — | 2.8 | — |
| Perlite abrasive | 6.5 | — | — | — | 22.5 | 0.5 |
| Sodium hydroxide | 0.8 | 1.6 | 1.8 | 0.8 | 1.1 | 1.0 |
| Carboxymethylcellulose | — | — | — | — | — | 2.6 |
| Pro-accord[1] | 1.0 | 1.0 | 1.0 | — | — | — |
| Pro-accord[2] | — | — | — | 1.0 | 1.0 | 1.2 |
| Minors/distilled water | bal. | bal. | bal. | bal. | bal. | bal. |

[1]Pro-accord according to Example 3.
[2]Pro-accord according to Example 7.

What is claimed is:

1. A composition for delivery of enduring fragrance or accord comprising:

a) from about 0.01% by weight, of a β-ketoester selected from the group consisting of 3,7-dimethyl-1,6-octadien-3-yl 3-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6dimethyl-7-octen-2-yl 3-(β-naphthyl)-3-oxo-propionate, 3,7dimethyl-1,6-octadien-3-yl 3-(4-methoxyphenyl)-3-oxo-propionate, (α,α-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3- oxo-propionate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof; and b) the balance comprising a carrier, said carrier selected from the group consisting of water, $C_1$–$C_3$ alcohols, $C_2$–$C_8$ poly hydroxy alcohols, water soluble cationic and anionic polymers, polyethylene glycols, and mixtures thereof.

2. A composition according to claim 1 wherein said carrier is ethanol.

3. A composition according to claim 1 wherein said carrier is a polyacrylate anionic polymer having an average molecular weight of less than about 20,000.

4. A composition according to claim 1 wherein said carrier is a copolymer of dimethyldiallyl ammonium chloride and acrylic acid.

5. A composition according to claim 1 further comprising a nonionic surfactant.

* * * * *

UNITED STATES PATENT AND TRADEMARK OFFICE
CERTIFICATE OF CORRECTION

PATENT NO. : 6,147,037
DATED : November 14, 2000
INVENTOR(S) : John Michael Gardlik et al.

It is certified that error appears in the above-identified patent and that said Letters Patent is hereby corrected as shown below:

Column 41, line 1 should read -- oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β -- .

Signed and Sealed this

First Day of May, 2001

Attest:

NICHOLAS P. GODICI

Attesting Officer      Acting Director of the United States Patent and Trademark Office